United States Patent [19]

Maurer et al.

[11] 4,120,956
[45] Oct. 17, 1978

[54] COMBATING ARTHROPODS WITH 3-ALKOXYMETHYL- AND-ALKYLTHIOMETHYL-PYRAZOL(-5)YL(THIONO)(THIOL)-PHOSPHORIC(-PHOSPHONIC) ACID ESTERS AND ESTER-AMIDES

[75] Inventors: Fritz Maurer; Hans-Jochem Riebel; Rolf Schröder, all of Wuppertal; Ingeborg Hammann, Cologne; Wolfgang Behrenz, Overath; Wilhelm Stendel, Wuppertal, all of Germany

[73] Assignee: Bayer Aktiengesellschaft, Leverkusen, Germany

[21] Appl. No.: 834,861

[22] Filed: Sep. 19, 1977

[30] Foreign Application Priority Data

Sep. 28, 1976 [DE] Fed. Rep. of Germany ....... 2643564

[51] Int. Cl.² .............. A01N 9/36; C07F 9/165; C07F 9/141; C07F 9/38
[52] U.S. Cl. .................. 424/200; 548/376; 548/377
[58] Field of Search .......... 548/376, 377; 424/200, 424/273 P

[56] References Cited

U.S. PATENT DOCUMENTS 2,754,244  7/1956  Gysin et al. .............. 424/200
3,010,969  11/1961 Rigterink ................. 424/200
3,825,557  7/1974  Hoffmann et al. .......... 548/376

*Primary Examiner*—Natalie Trousof
*Assistant Examiner*—Natalia Harkaway
*Attorney, Agent, or Firm*—Burgess, Dinklage & Sprung

[57] ABSTRACT

3-Alkoxymethyl- and -alkylthiomethyl-pyrazol(5)yl(thiono)(thiol)-phosphoric(phosphonic) acid esters and ester-amides of the formula

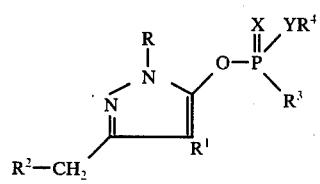

in which
R is hydrogen, alkyl, cyanoalkyl or phenyl,
$R^1$ is hydrogen or halogen,
$R^2$ is alkoxy or alkylthio,
$R^3$ is alkyl, alkoxy, monoalkylamino or phenyl,
$R^4$ is alkyl, and
X and Y each independently is oxygen or sulphur, which possess arthropodicidal properties.

10 Claims, No Drawings

COMBATING ARTHROPODS WITH 3-ALKOXYMETHYL- AND-ALKYLTHIOMETHYL-PYRAZOL(5)YL(THIONO)(THIOL)-PHOSPHORIC(PHOSPHONIC) ACID ESTERS AND ESTER-AMIDES

The present invention relates to and has for its objects the provision of particular new 3-alkoxymethyl- and -alkylthiomethyl-pyrazol(5)yl(thiono)(thiol)-phosphoric(phosphonic) acid esters and ester-amides which possess insecticidal properties, active compositions in the form of mixtures of such compounds with solid and liquid dispersible carrier vehicles, and methods for producing such compounds and for using such compounds in a new way especially for combating pests, e.g. arthropods, with other and further objects becoming apparent from a study of the within specification and accompanying examples.

It is known from U.S. Pat. No. 2,754,244 that certain O,O-dialkyl-O-pyrazolyl-thionophosphoric acid esters, such as O,O-diethyl-O-[3-methyl-pyrazol(5)yl]-thionophosphoric acid ester (compound A), possess insecticidal and acaricidal properties.

The present invention now provides, as new compounds, the alkoxymethyl-substituted and alkylthiomethyl-substituted pyrazolyl(thiono)(thiol)-phosphoric(phosphonic) acid esters and ester-amides of the general formula

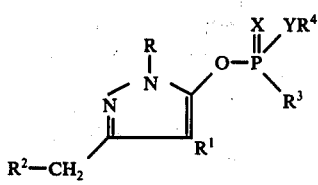
(I)

in which
R is hydrogen, alkyl, cyanoalkyl or phenyl,
$R^1$ is hydrogen or halogen,
$R^2$ is alkoxy or alkylthio,
$R^3$ is alkyl, alkoxy, monoalkylamino or phenyl,
$R^4$ is alkyl, and
X and Y each independently is oxygen or sulphur.

Preferably, R represents hydrogen, straight-chain or branched alkyl with 1 to 6 (especially 1 to 4) carbon atoms, straight-chain or branched cyanoalkyl with 1 to 4 carbon atoms in the alkyl part (especially cyanomethyl or 2-cyanoethyl) or phenyl, $R^1$ represents hydrogen or chlorine, $R^2$ represents straight-chain or branched alkoxy or alkylthio each with 1 to 6 (especially 1 to 4) carbon atoms, $R^3$ represents phenyl or straight-chain or branched alkyl, alkoxy or monoalkylamino each with 1 to 6 (especially 1 to 4) carbon atoms, $R^4$ represents straight-chain or branched alkyl with 1 to 6 (especially 1 to 4) carbon atoms, X represents sulphur and Y represents oxygen or sulphur.

Surprisingly, the alkoxymethyl-substituted and alkylthiomethyl-substituted pyrazolyl(thiono)(thiol)-phosphoric (phosphonic) acid esters and ester-amides according to the invention exhibit a better insecticidal and acaricidal action than the previously known O,O-dialkyl-O-pyrazolylthionophosphoric acid esters of analogous structure and of the same type of action. The compounds according to the present invention thus represent a genuine enrichment of the art.

The present invention also provides a process for the preparation of an alkoxymethyl-substituted and alkylthiomethyl-substituted pyrazolyl(thiono)(thiol)-phosphoric(phosphonic) acid ester or ester-amide of the formula (I), in which a (thiono)(thiol)-phosphoric(phosphonic) acid ester halide or ester-amide halide of the general formula

(II)

in which $R^3$, $R^4$, X and Y have the above-mentioned meanings and Hal represents halogen, preferably chlorine, is reacted, if appropriate in the presence of a solvent or diluent, with a 5-hydroxy-pyrazole of the general formula

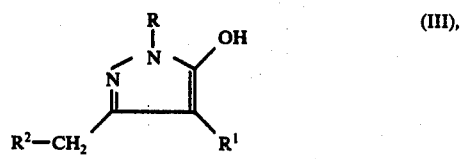
(III), in which R, $R^1$ and $R^2$ have the above-mentioned meanings, the latter being employed as such in the presence of an acid acceptor or in the form of an alkali metal salt, alkaline earth metal salt or ammonium salt.

If, for example, S-sec.-butyl-thionothiolethanephosphonic acid ester chloride and 1-ethyl-3-methylthiomethyl-5-hydroxy-pyrazole are used as starting materials, the course of the reaction can be represented by the following equation:

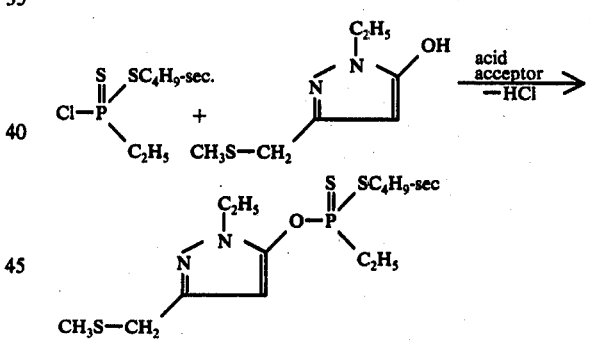

The (thiono)(thiol)-phosphoric(phosphonic) acid ester halides and ester-amide halides (II) required as starting materials are known and can readily be prepared according to customary processes. The following may be mentioned as individual examples: O,O-dimethyl-, O,O-diethyl-, O,O-di-n-propyl-, O,O-di-iso-propyl-, O,O-di-n-butyl-, O,O-di-iso-butyl-, O,O-di-sec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl- and O-iso-propyl-O-butyl-phosphoric acid diester chloride and the corresponding thiono analogues; O,S-dimethyl-, O,S-diethyl-, O,S-di-n-propyl-, O,S-di-iso-propyl-, O,S-di-n-butyl-, O,S-di-iso-butyl-, O-ethyl-S-n-propyl-, O-ethyl-S-isopropyl-, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S- ethyl-thiolphosphoric acid diester chloride and the corresponding thiono analogues; O-methyl-, O-ethyl-, O-n-propyl-, O-iso-propyl-, O-n-butyl-, O-iso-butyl- and O-sec.-butylmethane-, -ethane-, -n-propane-, -iso-propane-, -n-butane-, -iso-butane-, -tert.-butane-, -sec.-butane- and -phenylphosphonic acid ester chloride and the corresponding thiono analogues; S-methyl-, S-ethyl-, S-n-propyl-, S-iso-propyl-, S-n-butyl-, S-sec.-butyl and S-iso-butyl-methane-, ethane-, n-propane, iso-propane-, n-butane-, iso-butane-, sec.-butane- and phenylthiolphosphonic acid ester chloride and the corresponding thiono analogues; and O-methyl-N-methyl-, O-methyl-N-ethyl-, O-methyl-N-n-propyl, O-methyl-N-iso-propyl-, O-ethyl-N-methyl-, O-ethyl-N-ethyl-, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-iso-propyl-, O-iso-propyl-N-methyl-, O-isopropyl-N-ethyl-, O-iso-propyl-N-n-propyl-, O-iso-propyl-N-iso-propyl-, O-n-butyl-N-methyl-, O-n-butyl-N-ethyl, O-n-butyl-N-n-propyl-, O-n-butyl-N-iso-propyl-, O-iso-butyl-N-methyl-, O-iso-butyl-N-ethyl-, O-iso-butyl-N-n-propyl-, O-iso-butyl-N-iso-propyl-, O-sec.-butyl-N-methyl-, O-sec.-butyl-N-ethyl-, O-sec.-butyl-N-n-propyl- and O-sec.-butyl-N-iso-propyl-phosphoric acid monoester-amide chloride and the corresponding thionoanalogues.

The 5-hydroxy-pyrazoles (III), also required as starting materials, can be prepared in accordance with processes known from the literature, by reacting hydrazine derivatives with alkoxy-substituted or alkylthio-substituted acetoacetic acid alkyl esters. The following may be mentioned as individual examples: 3-methoxymethyl-, 3-ethoxymethyl-, 3-n-propoxymethyl-, 3-iso-propoxymethyl-, 3-n-butoxymethyl-, 3-iso-butoxymethyl-, 3-sec.-butoxymethyl-, 3-tert.-butoxymethyl-, 3-methylthiomethyl-, 3-ethylthiomethyl-, 3-n-propylthiomethyl-, 3-iso-propylthiomethyl-, 3-n-butylthiomethyl-, 3-iso-butylthiomethyl-, 3-sec.-butylthiomethyl- and 3-tert.-butylthiomethyl-5-hydroxypyrazole, as well as 3-methoxymethyl-4-chloro-, 3-ethoxymethyl-4-chloro-, 3-n-propoxymethyl-4-chloro-, 3-iso-propoxymethyl-4-chloro-, 3-n-butoxymethyl-4-chloro-, 3-iso-butoxymethyl-4-chloro-, 3-sec.-butoxymethyl-4-chloro-, 3-tert.-butoxymethyl-4-chloro-, 3-methylthiomethyl-4-chloro-, 3-ethylthiomethyl-4-chloro-, 3-n-propylthiomethyl-4-chloro-, 3-iso-propylthiomethyl-4-chloro-, 3-n-butylthiomethyl-4-chloro-, 3-iso-butylthiomethyl-4-chloro-, 3-sec.-butylthiomethyl-4-chloro- and 3-tert.-butylthiomethyl-4-chloro-5-hydroxy-pyrazole, 1-methyl-3-methoxymethyl-, 1-methyl-3-ethoxymethyl-, 1-methyl-3-n-propoxymethyl-, 1-methyl-3-iso-propoxymethyl-, 1-methyl-3-n-butoxymethyl-, 1-methyl-3-iso-butoxymethyl-, 1-methyl-3-sec.-butoxymethyl-, 1-methyl-3-tert.-butoxymethyl-, 1-methyl-3-methylthiomethyl-, 1-methyl-3-ethylthiomethyl-, 1-methyl-3-n-propylthiomethyl-, 1-methyl-3-n-butylthiomethyl-, 1-methyl-3-iso-butylthiomethyl-, 1-methyl-3-sec.-butylthio-methyl and 1-methyl-3-tert.-butylthiomethyl-5-hydroxy-pyrazole, 1-methyl-3-methoxymethyl-4-chloro-, 1-methyl-3-ethoxymethyl-4-chloro-, 1-methyl-3-n-propoxymethyl-4-chloro-, 1-methyl-3-iso-propoxymethyl-4-chloro-, 1-methyl-3-n-butoxymethyl-4-chloro-, 1-methyl-3-iso-butoxymethyl-4-chloro-, 1-methyl-3-sec.-butoxymethyl-4-chloro-, 1-methyl-3-tert.-butoxymethyl-4-chloro-, 1-methyl-3-methylthiomethyl-4-chloro-, 1-methyl-3-ethylthiomethyl-4-chloro-, 1-methyl-3-n-propylthiomethyl-4-chloro-, 1-methyl-3-iso-propylthiomethyl-4-chloro-, 1-methyl-3-n-butylthiomethyl-4-chloro-, 1-methyl-3-iso-butylthiomethyl-4-chloro-, 1-methyl-3-sec.-butylthiomethyl-4-chloro-, 1-methyl-3-tert.-butylthiomethyl-4-chloro-, 1-ethyl-3-methoxymethyl-, 1-ethyl-3-ethoxymethyl-, 1-ethyl-3-n-propoxymethyl-, 1-ethyl-3-iso-propoxymethyl-, 1-ethyl-3-n-butoxymethyl-, 1-ethyl-3-iso-butoxymethyl-, 1-ethyl-3-sec.-butoxymethyl-, 1-ethyl-3-tert.-butoxymethyl-, 1-ethyl-3-methylthiomethyl-, 1-ethyl-3-ethylthiomethyl-, 1-ethyl-3-n-propylthiomethyl-, 1-ethyl-3-iso-propylthiomethyl-, 1-ethyl-3-n-butylthiomethyl-, 1-ethyl-3-iso-butylthiomethyl-, 1-ethyl-3-sec.-butylthiomethyl- and 1-ethyl-3-tert.-butylthiomethyl-5-hydroxy-pyrazole, 1-ethyl-3-methoxymethyl-4-chloro-, 1-ethyl-3-ethoxymethyl-4-chloro-, 1-ethyl-3-n-propoxymethyl-4-chloro-, 1-ethyl-3-iso-propoxymethyl-4-chloro-, 1-ethyl-3-n-butoxymethyl-4-chloro-, 1-ethyl-3-iso-butoxymethyl-4-chloro-, 1-ethyl-3-sec.-butoxymethyl-4-chloro-, 1-ethyl-3-tert.-butoxymethyl-4-chloro-, 1-ethyl-3-methylthiomethyl-4-chloro-, 1-ethyl-3-ethylthiomethyl-4-chloro-, 1-ethyl-3-n-propylthiomethyl-4-chloro-, 1-ethyl-3-iso-propylthiomethyl-4-chloro-, 1-ethyl-3-n-butylthiomethyl-4-chloro-, 1-ethyl-3-iso-butylthiomethyl-4-chloro-, 1-ethyl-3-sec.-butylthiomethyl-4-chloro- and 1-ethyl-3-tert.-butylthiomethyl-4-chloro-5-hydroxy-pyrazole, 1-n-propyl-3-methoxymethyl-, 1-n-propyl-3-ethoxymethyl-, 1-n-propyl-3-n-propoxymethyl-, 1-n-propyl-3-iso-propoxymethyl-, 1-n-propyl-3-n-butoxymethyl-, 1-n-propyl-3-iso-butoxymethyl-, 1-n-propyl-3-sec.-butoxymethyl-, 1-n-propyl-3-tert.-butoxymethyl-, 1-n-propyl-3-methylthiomethyl-, 1-n-propyl-3-ethylthiomethyl-, 1-n-propyl-3-n-propylthiomethyl-, 1-n-propyl-3-iso-propylthiomethyl-, 1-n-propyl-3-n-butylthiomethyl-, 1-n-propyl-3-iso-butylthiomethyl-, 1-n-propyl-3-sec.-butylthiomethyl- and 1-n-propyl-3-tert.-butylthiomethyl-5-hydroxy-pyrazole, 1-n-propyl-3-methoxymethyl-4-chloro, 1-n-propyl-3-ethoxymethyl-4-chloro-, 1-n-propyl-3-n-propoxymethyl-4-chloro-, 1-n-propyl-3-iso-propoxymethyl-4-chloro-, 1-n-propyl-3-n-butoxymethyl-4-chloro-, 1-n-propyl-3-iso-butoxymethyl-4-chloro-, 1-n-propyl-3-sec.-butoxymethyl-4-chloro-, 1-n-propyl-3-tert.-butoxymethyl-4-chloro-, 1-n-propyl-3-methylthiomethyl-4-chloro-, 1-n-propyl-3-ethylthiomethyl-4-chloro-, 1-n-propyl-3-n-propylthiomethyl-4-chloro-, 1-n-propyl-3-iso-propylthiomethyl-4-chloro-, 1-n-propyl-3-n-butylthiomethyl-4-chloro-, 1-n-propyl-3-iso-butylthiomethyl-4-chloro-, 1-n-propyl-3-sec.-butylthiomethyl-4-chloro- and 1-n-propyl-3-tert.-butylthiomethyl-4-chloro-5-hydroxy-pyrazole, 1-iso-propyl-3-methoxymethyl-, 1-iso-propyl-3-ethoxymethyl-, 1-iso-propyl-3-n-propoxymethyl-, 1-iso-propyl-3-iso-propoxymethyl-, 1-iso-propyl-3-n-butoxymethyl-, 1-iso-propyl-3-iso-butoxymethyl-, 1-iso-propyl-3-sec.-butoxymethyl-, 1-iso-propyl-3-tert.-butoxymethyl-, 1-iso-propyl-3-methylthiomethyl-, 1-iso-propyl-3-ethylthiomethyl-, 1-iso-propyl-3-n-propylthiomethyl-, 1-iso-propyl-3-iso-propylthiomethyl-, 1-iso-propyl-3-n-butylthiomethyl-, 1-iso-propyl-3-iso-butylthiomethyl-, 1-iso-propyl-3-sec.-butylthiomethyl- and 1-iso-propyl-3-tert.-butylthiomethyl-5-hydroxy-pyrazole, 1-iso-propyl-3-methoxymethyl-4-chloro-, 1-iso-propyl-3-ethoxymethyl-4-chloro-, 1-iso-propyl-3-n-propoxymethyl-4-chloro-, 1-iso-propyl-3-iso-propoxymethyl-4-chloro-, 1-iso-propyl-3-n-butoxymethyl-4-chloro-, 1-iso-propyl-3-iso-butoxymethyl-4-chloro-, 1-iso-propyl-3-sec.-butoxymethyl-4-chloro-, 1-iso-propyl-3-tert.-butoxymethyl-4-chloro-, 1-iso-propyl-3-methylthiomethyl-4-chloro-, 1-iso-propyl-3-ethylthiomethyl-4-chloro-, 1-iso-propyl-3-n-propylthiomethyl-4-chloro-, 1-iso-propyl-3-iso-propylthiomethyl-4-chloro-, 1-iso-propyl-3-n-butylthiomethyl-4-chloro-, 1-iso-propyl-3-iso-butylthiomethyl-4-chloro-, 1-iso-propyl-3-sec.-butylthiomethyl-4-chloro- and 1-iso-propyl-3-tert.-butylthiomethyl-4-chloro-5-hydroxy-pyrazole, and also 1-n-butyl-3-methoxymethyl-, 1-n-butyl-3-ethoxymethyl-, 1-n-butyl-3-n-propoxymethyl-, 1-n-butyl-3-iso-propoxymethyl-, 1-n-butyl-3-n-butoxymethyl-, 1-n-butyl-3-iso-butoxymethyl-, 1-n-butyl-3-sec.-butoxymethyl-, 1-n-butyl-3-tert.-butoxymethyl-, 1-n-butyl-3-methylthiomethyl-, 1-n-butyl-3-ethylthiomethyl-, 1-n-butyl-3-n-propylthiomethyl-, 1-n-butyl-3-iso-propylthiomethyl-, 1-n-butyl-3-n-butylthiomethyl-, 1-n-butyl-3-iso-butylthiomethyl-, 1-n-butyl-3-sec.-butylthiomethyl- and 1-n-butyl-3-tert.-butylthiomethyl-5-hydroxypyrazole, 1-n-butyl-3-methoxymethyl-4-chloro-, 1-n-butyl-3-ethoxymethyl-4-chloro-, 1-n-butyl-3-n-propoxymethyl-4-chloro-, 1-n-butyl-3-iso-propoxymethyl-4-chloro-, 1-n-butyl-3-n-butoxymethyl-4-chloro-, 1-n-butyl-3-iso-butoxymethyl-4-chloro-, 1-n-butyl-3-sec.-butoxymethyl-4-chloro-, 1-n-butyl-3-tert.-butoxymethyl-4-chloro-, 1-n-butyl-3-methylthiomethyl-4-chloro-, 1-n-butyl-3-ethylthiomethyl-4-chloro-, 1-n-butyl-3-n-propylthiomethyl-4-chloro-, 1-n-butyl-3-iso-propylthiomethyl-4-chloro-, 1-n-butyl-3-n-butylthiomethyl-4-chloro-, 1-n-butyl-3-iso-butylthiomethyl-4-chloro-, 1-n-butyl-3-sec.-butylthiomethyl-4-chloro- and 1-n-butyl-3-tert.-butylthiomethyl-4-chloro-5-hydroxy-pyrazole, 1-iso-butyl-3-methoxymethyl-, 1-iso-butyl-3-ethoxymethyl-, 1-iso-butyl-3-n-propoxymethyl-, 1-iso-butyl-3-iso-propoxymethyl-, 1-iso-butyl-3-n-butoxymethyl-, 1-iso-butyl-3-iso-butoxymethyl-, 1-iso-butyl-3-sec.-butoxymethyl-, 1-iso-butyl-3-tert.-butoxymethyl-, 1-iso-butyl-3-methylthiomethyl-, 1-iso-butyl-3-ethylthiomethyl-, 1-iso-butyl-3-n-propylthiomethyl-, 1-iso-butyl-3-iso-propylthiomethyl-, 1-iso-butyl-3-n-butylthiomethyl-, 1-iso-butyl-3-isobutylthiomethyl-, 1-iso-butyl-3-sec.-butylthiomethyl- and 1-iso-butyl-3-tert.-butylthiomethyl-5-hydroxy-pyrazole, 1-iso-butyl-3-methoxymethyl-4-chloro-, 1-iso-butyl-3-methoxymethyl-4-chloro-, 1-iso-butyl-3-n-propoxymethyl-4-chloro-, 1-iso-butyl-3-iso-propoxymethyl-4-chloro-, 1-iso-butyl-3-n-butoxymethyl-4-chloro-, 1-iso-butyl-3-iso-butoxymethyl-4-chloro-, 1-iso-butyl-3-sec.-butoxymethyl-4-chloro-, 1-iso-butyl-3-tert.-butoxymethyl-4-chloro-, 1-iso-butyl-3-methylthiomethyl-4-chloro-, 1-iso-butyl-3-ethylthiomethyl- 4-chloro-, 1-iso-butyl-3-n-propylthiomethyl-4-chloro-, 1-iso-butyl-3-iso-propylthiomethyl-4-chloro-, 1-iso-butyl-3-n-butylthiomethyl-4-chloro-, 1-iso-butyl-3-iso-butylthiomethyl-4-chloro-, 1-iso-butyl-3-sec.-butylthiomethyl-4-chloro- and 1-iso-butyl-3-tert.-butylthiomethyl-4-chloro-5-hydroxy-pyrazole, 1-sec.-butyl-3-methoxymethyl-, 1-sec.-butyl-3-ethoxymethyl-, 1-sec.-butyl-3-n-propoxymethyl-, 1-sec.-butyl-3-iso-propoxymethyl-, 1-sec.-butyl-3-n-butoxymethyl-, 1-sec.-butyl-3-iso-butoxymethyl-, 1-sec.-butyl-3-sec.-butoxymethyl-, 1-sec.-butyl-3-tert.-butoxymethyl-, 1-sec.-butyl-3-methylthiomethyl-, 1-sec.-butyl-3-ethylthiomethyl-, 1-sec.-butyl-3-n-propylthiomethyl-, 1-sec.-butyl-3-iso-propylthiomethyl-, 1-sec.-butyl-3-n-butylthiomethyl-, 1-sec.-butyl-3-iso-butylthiomethyl-, 1-sec.-butyl-3-sec.-butylthiomethyl- and 1-sec.-butyl-3-tert.-butylthiomethyl-5-hydroxy-pyrazole, 1-sec.-butyl-3-methoxymethyl-4-chloro-, 1-sec.-butyl-3-ethoxymethyl-4-chloro-, 1-sec.-butyl-3-n-propoxymethyl-4-chloro-, 1-sec.-butyl-3-iso-propoxymethyl-4-chloro-, 1-sec.-butyl-3-n-butoxymethyl-4-chloro-, 1-sec.-butyl-3-iso-butoxymethyl-4-chloro, 1-sec.-butyl-3-tert.-butoxymethyl-4-chloro-, 1-sec.-butyl-3-methylthiomethyl-4-chloro-, 1-sec.-butyl-3-ethylthiomethyl-4-chloro-, 1-sec.-butyl-3-n-propylthiomethyl-4-chloro-, 1-sec.-butyl-3-iso-propylthiomethyl-4-chloro-, 1-sec.-butyl-3-n-butylthiomethyl-4-chloro-, 1-sec.-butyl-3-iso-butylthiomethyl-4-chloro-, 1-sec.-butyl-3-sec.-butylthiomethyl-4-chloro- and 1-sec.-butyl-3-tert.-butylthiomethyl-4-chloro-5-hydroxy-pyrazole, 1-tert.-butyl-3-methoxymethyl-, 1-tert.-butyl-3-ethoxymethyl-, 1-tert.-butyl-3-n-propoxymethyl-, 1-tert.-butyl-3-iso-propoxymethyl-, 1-tert.-butyl-3-n-butoxymethyl-, 1-tert.-butyl-3-iso-butoxymethyl-, 1-tert.-butyl-3-sec.-butoxymethyl-, 1-tert.-butyl-3-tert.-butoxymethyl-, 1-tert.-butyl-3-methylthiomethyl-, 1-tert.-butyl-3-ethylthiomethyl-, 1-tert.-butyl-3-n-propylthiomethyl-, 1-tert.-butyl-3-iso-propylthiomethyl-, 1-tert.-butyl-3-n-butylthiomethyl-, 1-tert.-butyl-3-iso-butylthiomethyl-, 1-tert.-butyl-3-sec.-butylthiomethyl- and 1-tert.-butyl-3-tert.-butylthiomethyl-5-hydroxy-pyrazole, 1-tert.-butyl-3-methoxymethyl-4-chloro-, 1-tert.-butyl-3-ethoxymethyl-4-chloro-, 1-tert.-butyl-3-n-propoxymethyl-4-chloro-, 1-tert.-butyl-3-iso-propoxymethyl-4-chloro-, 1-tert.-butyl-3-n-butoxymethyl-4-chloro-, 1-tert.-butyl-3-iso-butoxymethyl-4-chloro-, 1-tert.-butyl-3-sec.-butoxymethyl-4-chloro-, 1-tert.-butyl-3-tert.-butoxymethyl-4-chloro-, 1-tert.-butyl-3-methylthiomethyl-4-chloro-, 1-tert.-butyl-3-ethylthiomethyl-4-chloro-, 1-tert.-butyl-3-n-propylthiomethyl-4-chloro-, 1-tert.-butyl-3-iso-propylthio-methyl-4-chloro-, 1-tert.-butyl-3-n-butylthiomethyl-4-chloro-, 1-tert.-butyl-3-iso-butylthiomethyl-4-chloro-, 1-tert.-butyl-3-sec.-butylthiomethyl-4-chloro- and 1-tert.-butyl-3-tert.-butylthiomethyl-4-chloro-5-hydroxy-pyrazole, 1-phenyl-3-methoxymethyl-, 1-phenyl-3-ethoxymethyl-, 1-phenyl-3-n-propoxymethyl-, 1-phenyl-3-isopropoxymethyl-, 1-phenyl-3-n-butoxymethyl-, 1-phenyl-3-isobutoxymethyl-, 1-phenyl-3-sec.-butoxymethyl-, 1-phenyl-3-tert.-butoxymethyl-, 1-phenyl-3-methylthiomethyl-, 1-phenyl-3-ethylthiomethyl-, 1-phenyl-3-n-propylthiomethyl-, 1-phenyl-3-iso-propylthiomethyl-, 1-phenyl-3-n-butylthiomethyl-, 1-phenyl-3-iso-butylthiomethyl-, 1-phenyl-3-sec.-butylthiomethyl- and 1-phenyl-3-tert.-butylthiomethyl-5-hydroxypyrazole, 1-phenyl-3-methoxymethyl-4-chloro, 1-phenyl-3-ethoxymethyl-4-chloro, 1-phenyl-3-n-propoxymethyl-4-chloro-, 1-phenyl-3-iso-propoxymethyl-4-chloro-, 1-phenyl-3-n-butoxymethyl-4-chloro-, 1-phenyl-3-isobutoxymethyl-4-chloro-, 1-phenyl-3-sec.-butoxymethyl-4-chloro-, 1-phenyl-3-tert.-butoxymethyl-4-chloro-, 1-phenyl-3-methylthiomethyl-4-chloro-, 1-phenyl-3-ethylthiomethyl-4-chloro, 1-phenyl-3-n-propylthiomethyl-4-chloro-, 1-phenyl-3-iso-propylthiomethyl-4-chloro-, 1-phenyl-3-n-butylthiomethyl-4-chloro-, 1-phenyl-3-isobutylthiomethyl-4-chloro-, 1-phenyl-3-sec.-butylthiomethyl-4-chloro- and 1-phenyl-3-tert.-butylthiomethyl-4-chloro-5-hydroxy- pyrazole, 1-cyanomethyl-3-methoxymethyl-, 1-cyanomethyl-3-ethoxymethyl-, 1-cyanomethyl-3-n-propoxymethyl-, 1-cyanomethyl-3-iso-propoxymethyl-, 1-cyanomethyl-3-n-butoxymethyl-, 1-cyanomethyl-3-iso-butoxymethyl-, 1-cyanomethyl-3-sec.-butoxymethyl-, 1-cyanomethyl-3-tert.-butoxymethyl-, 1-cyanomethyl-3-methylthiomethyl-, 1-cyanomethyl-3-ethylthiomethyl-, 1-cyanomethyl-3-n-propylthiomethyl-, 1-cyanomethyl-3-iso-propylthiomethyl-, 1-cyanomethyl-3-n-butylthiomethyl-, 1-cyanomethyl-3-iso-butylthiomethyl-, 1-cyanomethyl-3-sec.-butylthiomethyl- and 1-cyanomethyl-3-tert.-butylthiomethyl-5-hydroxypyrazole, 1-cyanomethyl-3-methoxymethyl-4-chloro-, 1- cyanomethyl-3-ethoxymethyl-4-chloro-, 1-cyanomethyl-3-n-propoxymethyl-4-chloro-, 1-cyanomethyl-3-iso-propoxymethyl-4-chloro-, 1-cyanomethyl-3-n-butoxymethyl-4-chloro-, 1-cyanomethyl-3-iso-butoxymethyl-4-chloro-, 1-cyanomethyl-3-sec.-butoxymethyl-4-chloro-, 1-cyanomethyl-3-tert.-butoxymethyl-4-chloro-, 1-cyanomethyl-3-methylthiomethyl-4-chloro-, 1-cyanomethyl-3-ethylthiomethyl-4-chloro-, 1-cyanomethyl-3-n-propylthiomethyl-4-chloro-, 1-cyanomethyl-3-iso-propylthiomethyl-4-chloro-, 1-cyanomethyl-3-n-butylthiomethyl-4-chloro-, 1-cyanomethyl-3-iso-butylthiomethyl-4-chloro-, 1-cyanomethyl-3-sec.-butylthiomethyl-4-chloro- and 1-cyanomethyl-3-tert.-butylthiomethyl-4-chloro-5-hydroxypyrazole, 1-(2-cyanoethyl)-3-methoxymethyl-, 1-(2-cyanoethyl)-3-ethoxymethyl-, 1-(2-cyanoethyl)-3-n-propoxymethyl-, 1-(2-cyanoethyl)-3-iso-propoxymethyl-, 1-(2-cyanoethyl)-3-n-butoxymethyl-, 1-(2-cyanoethyl)-3-iso-butoxymethyl-, 1-(2-cyanoethyl)-3-sec.-butoxymethyl-, 1-(2-cyanoethyl)-3-tert.-butoxymethyl-, 1-(2-cyanoethyl)-3-methylthiomethyl-, 1-(2-cyanoethyl)-3-ethylthiomethyl-, 1-(2-cyanoethyl)-3-n-propylthiomethyl-, 1-(2-cyanoethyl)-3-iso-propylthiomethyl-, 1-(2-cyanoethyl)-3-n-butylthiomethyl-, 1-(2-cyanoethyl)-3-iso-butylthiomethyl-, 1-(2-cyanoethyl)-3-sec.-butylthiomethyl- and 1-(2-cyanoethyl)-3-tert.-butylthiomethyl-5-hydroxy-pyrazole, 1-(2-cyanoethyl)-3-methoxymethyl-4-chloro-, 1-(2-cyanoethyl)-3-ethoxymethyl-4-chloro-, 1-(2-cyanoethyl)-3-n-propoxymethyl-4-chloro-, 1-(2-cyanoethyl)-3-iso-propoxymethyl-4-chloro-, 1-(2-cyanoethyl)-3-n-butoxymethyl-4-chloro-, 1-(2-cyanoethyl)-3-iso-butoxymethyl-4-chloro-, 1-(2-cyanoethyl)-3-sec.-butoxymethyl-4-chloro-, 1-(2-cyanoethyl)-3-tert.-butoxymethyl-4-chloro-, 1-(2-cyanoethyl)-3-methylthiomethyl-4-chloro-, 1-(2-cyanoethyl)-3-ethylthiomethyl-4-chloro-, 1-(2-cyanoethyl)-3-n-propylthiomethyl-4-chloro-, 1-(2-cyanoethyl)-3-iso-propylthiomethyl-4-chloro-, 1-(2-cyanoethyl)-3-n-butylthiomethyl-4-chloro-, 1-(2-cyanoethyl)-3-iso-butylthiomethyl-4-chloro-, 1-(2-cyanoethyl)-3-sec.-butylthiomethyl-4-chloro-and 1-(2-cyanoethyl)-3-tert.-butylthiomethyl-4-chloro-5-hydroxy-pyrazole.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate and tert.-butylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at from 0° to 100° C. preferably at from 20° to 60° C.

In general, the reaction is allowed to take place under normal pressure.

To carry out the process, the starting materials are preferably employed in equimolar amounts. An excess of one or other reactant produces no significant advantages.

Preferably, the 5-hydroxy-pyrazole (III) and the acid acceptor are first introduced into a solvent and this suspension is stirred at an elevated temperature. After cooling, the phosphoric acid ester derivative (II) is added to the mixture and the latter is worked up, after completion of the reaction, in the usual manner by adding water and an organic solvent to the reaction solution, separating off the organic phase, drying it and evaporating off the solvent.

The new compounds are obtained in the form of oils, which in most cases cannot be distilled without decomposition, but are freed from the last volatile constituents by so-called "slight distillation", that is to say by prolonged heating under reduced pressure to moderately elevated temperatures, and are purified in this way.

As already mentioned, the compounds according to the present invention are distinguished by an excellent insecticidal and acaricidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine, since they are also active against animal parasites, in particular ectoparasites such as parasitic fly larvae and scab mites.

The active compounds are well tolerated by plants, have a favorable level of toxicity to warm-blooded animals, and can be used for combating arthropod pests, especially insects and arachnids, which are encountered in agriculture, in forestry, in the protection of stored products and of materials, and in the hygiene field. They are active against normally sensitive and resistant species and against all or some stages of development. The above-mentioned pests include:

from the class of the *Isopoda*, for example *Oniscus asellus, Armadillidium vulgare* and *Porcellio scaber;* from the class of the *Diplopoda*, for example *Blaniulus guttulatus;* from the class of the *Chilopoda*, for example *Geophilus carpophagus* and *Scutigera* spec.;

from the class of the *Symphyla*, for example *Scutigerella immaculata;* from the order of the *Thysanura*, for example *Lepisma saccharina;* from the order of the *Collembola*, for example *Onychiurus armatus;* from the order of the *Orthoptera*, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the *Dermaptera*, for example *Forficula auricularia;* from the order of the *Isoptera*, for example *Reticulitermes* spp.;

from the order of the *Anoplura*, for example *Phylloxera vastatrix, Pemphigus* spp., *Pediculus humanus corporis, Haematopinus* spp. and *Linognathus* spp.;

from the order of the *Mallophaga*, for example *Trichodectes* spp. and *Damalinea* spp.;

from the order of the *Thysanoptera*, for example *Hercinothrips femoralis* and *Thrips tabaci;* from the order of the *Heteroptera*, for example *Eurygaster* spp., *Dysdercus intermedius, Piesma quadrata, Cimex lectularius, Rhodnius prolixus* and *Triatoma* spp.;

from the order of the *Homoptera*, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

from the order of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Pryllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the *Hymenoptera*, for example *Diprion* spp., *Hoplocampa* spp., *Monomorium pharaonis* and *Vespa* spp.;

from the order of the *Diptera*, for example *Aedes* spp., *Anopheles* spp., *Culex* spp., *Drosophila melanogaster, Musca* spp., *Fannia* spp., *Calliphora erythrocephala, Lucilia* spp., Chrysomyia spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the *Siphonaptera*, for example *Xenopsylla cheopis* and *Ceratophyllus* spp.;

from the class of the *Arachnida*, for example *Scorpio maurus* and *Latrodectus mactans;* from the order of the *Acarina*, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. etone, methyl ethyl ketone methyl isobutyl ketone; cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl aryl-polyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplate overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

The starting materials required for the preparation of the compounds according to the invention were prepared, for example, as described below:

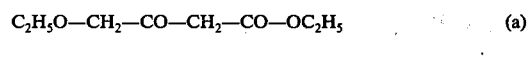
(a)

1st stage 72 g (1 mol) of chlorine were passed into a solution of 84 g (1 mol) of diketene in dry carbon tetrachloride at −20° C., the reaction solution was then added dropwise to 200 ml of ethanol, while stirring, during which addition the temperature was held to at most 0° C., the solvent was then stripped off in vacuo on a rotary evaporator and the residue was distilled. 155 g (94% of theory) of γ-chloroacetoacetic acid ethyl ester of boiling point 90° C./7 mm Hg were obtained.

2nd stage 2.2 mol of sodium ethylate in ethanol — prepared from 55.2 g (2.2 mols) of sodium and 500 ml of ethanol — were diluted with 500 ml of tetrahydrofuran. 164.5 g (1 mol) of γ-chloroacetoacetic acid ethyl ester were added to the solution, at room temperature, sufficiently rapidly that the reaction temperature rose to 50° C. The mixture was then cooled to room temperature, 72 g (1.2 mols) of glacial acetic acid were added, the solvent was evaporated off on a rotary evaporator in vacuo, the residue was shaken with 200 ml of water, the mixture was extracted twice with 250 ml of methylene chloride each time, and the combined organic phases were dried over magnesium sulphate. The solvent was stripped off in vacuo and the residue was distilled. 123.7 g (71% of theory) of γ-ethoxyacetoacetic acid ethyl ester of boiling point 75° C./3 mm Hg were obtained.

γ-Methoxyacetoacetic acid methyl ester, of boiling point ~ 76° C./7 mm Hg, was prepared analogously, in a yield of 63% of theory.

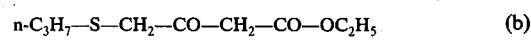
(b)

367 g (2.3 mols) of bromine were added dropwise over the course of 90 minutes, at 0° C., to a solution of 300 g (2.3 mols) of acetoacetic acid ethyl ester in 350 ml of ether, the mixture was then stirred for a further hour at room temperature, 500 ml of water were added while cooling with ice, the phases were separated and the ether phase was washed once with 100 ml of a 10% strength sodium bicarbonate solution. After drying over magnesium sulphate, the ether phase was added dropwise, at room temperature, to a solution, in ethanol, of 2 mols of sodium propylmercaptide, prepared from 46 g (2 mols) of sodium, 600 g of ethanol and 152 g (2 mols) of propylmercaptan; the batch was stirred for a further hour at room temperature and was then extracted by shaking with 2 mols of sodium hydroxide solution (1,334 g of a 6% strength solution), the ether phase was discarded, the aqueous phase was acidified to pH ∼ 2 with concentrated hydrochloric acid and was extracted by shaking 3 times with 300 ml of methylene chloride each time, the combined organic phases were dried over magnesium sulphate and the solvent was distilled off. After distilling the residue, 200 g (50% of theory) of γ-propylmercaptoacetoacetic acid ethyl ester of boiling point ∼ 85° C./0.7 mm Hg were obtained.

The following were prepared analogously:
γ-Methylmercaptoacetoacetic acid ethyl ester, of boiling point 100° C./2 mm Hg, in 49% yield.
γ-Ethylmercaptoacetoacetic acid ethyl ester, of boiling point 99° C./1 mm Hg, in 56% yield.

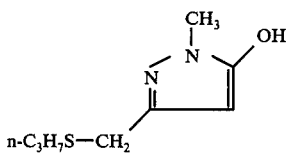

(c)

9.2 g (0.2 mol) of methylhydrazine were added dropwise to a solution of 38 g (0.2 mol) of γ-propylthioacetoacetic acid methyl ester in 150 ml of ethanol at a rate such that the temperature rose to 55°-60° C., and the mixture was then stirred for a further hour at 60° C. To work up the reaction solution, the solvent was completely distilled off on a rotary evaporator in vacuo and the crystalline residue was stirred with 250 ml of ether, filtered off and dried. 24 g (65% of theory) of 1-methyl-3-n-propylthiomethyl-5-hydroxypyrazole remained in the form of colorless crystals of melting point 108°-110° C.

The following compounds of the formula

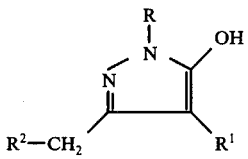

(III)

could be prepared analogously:

Table 1

| R | $R^1$ | $R^2$ | Yield (% of theory) | Physical data (melting point; ° C; refractive index |
|---|---|---|---|---|
| H | H | $CH_3O$ | 86 | 95 – 98 |
| $CH_3$ | H | $CH_3O$ | 73 | 87 |
| $CH_3$ | H | $C_2H_5O$ | 68 | 97 |
| $C_3H_7$-iso | H | $CH_3O$ | 87 | $n_D^{23}$:1.4900 |
| –⟨phenyl⟩ | H | $C_2H_5O$ | 98 | $n_D^{23}$:1.5310 |
| –$CH_2$–$CH_2$–CN | H | $CH_3O$ | 88 | 78 – 80 |
| $C_3H_7$-iso | H | n-$C_3H_7S$ | 80 | 91 |
| $CH_3$ | H | $CH_3S$ | 86 | 130 |
| $CH_3$ | H | $C_2H_5S$ | 83 | 114 |

EXAMPLE 2

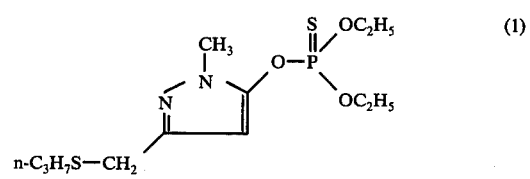

(1)

A suspension of 9.3 g (50 mmols) of 1-methyl-3-n-propylthiomethyl-5-hydroxypyrazole, 8.4 g (60 mmols) of ground potassium carbonate and 200 ml of acetonitrile was stirred for one hour at 50° C. and was then cooled to room temperature, and 8.6 g (50 mmols) of O-ethyl-ethanethionophosphonic acid ester chloride were added. After stirring for one hour at 50° C., the reaction solution was extracted by shaking with 200 ml of water and with 300 ml of toluene. The organic phase was dried over magnesium sulphate and after filtration the toluene was stripped off on a rotary evaporator in vacuo. 14 g (87% of theory) of O-ethyl-O-[1-methyl-3-n-propylthiomethylpyrazol(5)yl]-thionoethanephosphonic acid ester remained in the form of a yellow oil having a refractive index $n_D^{23}$ of 1.5220.

The following compounds of the formula

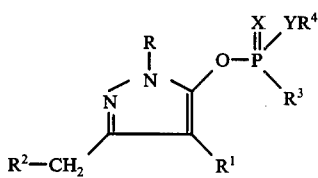

(I)

could be synthesized analogously:

Table 2

| Compound No. | R | $R^1$ | $R^2$ | $R^3$ | $R^4$ | X | Y | Yield (% of theory) | Refractive index: |
|---|---|---|---|---|---|---|---|---|---|
| 2 | $CH_3$ | H | n-$C_3H_7S$ | $OC_2H_5$ | $C_2H_5$ | S | O | 83 | $n_D^{23}$:1.5095 |
| 3 | $CH_3$ | H | n-$C_3H_7S$ | $OCH_3$ | $CH_3$ | S | O | 90 | $n_D^{23}$:1.5246 |
| 4 | $CH_3$ | H | n-$C_3H_7S$ | $CH_3$ | $C_4H_9$-sec. | S | S | 74 | $n_D^{23}$:1.5450 |
| 5 | $CH_3$ | H | n-$C_3H_7S$ | $CH_3$ | $C_3H_7$-iso | S | O | 93 | $n_D^{23}$:1.5060 |
| 6 | $CH_3$ | H | n-$C_3H_7S$ | –⟨phenyl⟩ | $C_2H_5$ | S | O | 83 | $n_D^{23}$:1.5650 |
| 7 | $CH_3$ | H | n-$C_3H_7S$ | $OC_2H_5$ | $C_2H_5$ | O | O | 87 | $n_D^{23}$:1.4849 |
| 8 | $CH_3$ | H | n-$C_3H_7S$ | $CH_3$ | $C_2H_5$ | S | O | 93 | $n_D^{23}$:1.5242 |
| 9 | $CH_3$ | H | n-$C_3H_7S$ | $OC_2H_5$ | $C_3H_7$-n | S | O | 86 | $n_D^{23}$:1.5043 |
| 10 | $CH_3$ | H | n-$C_3H_7S$ | $OCH_3$ | $C_3H_7$-n | S | O | 92 | $n_D^{23}$:1.5089 |

Table 2-continued

| Compound No. | R | R¹ | R² | R³ | R⁴ | X | Y | Yield (% of theory) | Refractive index: |
|---|---|---|---|---|---|---|---|---|---|
| 11 | CH₃ | H | n-C₃H₇S | OC₃H₇-iso | C₃H₇-n | S | O | 94 | $n_D^{23}$:1.5010 |
| 12 | CH₃ | H | CH₃O | C₂H₅ | C₂H₅ | S | O | 90 | $n_D^{23}$:1.5072 |
| 13 | CH₃ | H | CH₃O | CH₃ | C₄H₉-sec. | S | S | 73 | $n_D^{23}$:1.5423 |
| 14 | CH₃ | H | CH₃O | OC₂H₅ | C₂H₅ | S | O | 73 | $n_D^{23}$:1.4920 |
| 15 | CH₃ | H | CH₃O | OC₂H₅ | C₃H₇-n | S | S | 77 | $n_D^{23}$:1.5222 |
| 16 | CH₃ | H | CH₃O | OC₂H₅ | C₂H₅ | S | O | 92 | $n_D^{23}$:1.5545 |
| 17 | CH₃ | H | CH₃O | CH₃ | C₃H₇-iso | S | O | 99 | $n_D^{23}$:1.5050 |
| 18 | CH₃ | H | CH₃O | OC₂H₅ | C₂H₅ | O | O | 74 | $n_D^{23}$:1.4621 |
| 19 | CH₃ | H | CH₃O | OCH₃ | CH₃ | S | O | 99 | $n_D^{23}$:1.5001 |
| 20 | CH₃ | H | CH₃O | CH₃ | C₂H₅ | S | O | 95 | $n_D^{23}$:1.5130 |
| 21 | CH₃ | H | CH₃O | C₂H₅ | CH₃ | S | O | 91 | $n_D^{23}$:1.5153 |
| 22 | CH₃ | H | CH₃O | OC₂H₅ | C₃H₇-n | S | O | 97 | $n_D^{23}$:1.4912 |
| 23 | CH₃ | H | CH₃O | OC₃H₇-iso | C₃H₇-n | S | O | 86 | $n_D^{23}$:1.4854 |
| 24 | CH₃ | H | CH₃O | OCH₃ | C₃H₇-n | S | O | 77 | $n_D^{23}$:1.4930 |
| 25 | CH₃ | H | CH₃O | NH—C₃H₇-iso | C₂H₅ | S | O | 82 | $n_D^{23}$:1.5094 |
| 26 | CH₃ | H | CH₃O | C₄H₉-sec. | C₂H₅ | S | O | 85 | $n_D^{23}$:1.5072 |
| 27 | CH₃ | H | C₂H₅O | C₂H₅ | C₂H₅ | S | O | 99 | $n_D^{20}$:1.5041 |
| 28 | CH₃ | H | C₂H₅O | CH₃ | C₄H₉-sec. | S | S | 78 | $n_D^{20}$:1.5354 |
| 29 | CH₃ | H | C₂H₅O | OC₂H₅ | C₂H₅ | S | O | 87 | $n_D^{20}$:1.4920 |
| 30 | CH₃ | H | C₂H₅O | OC₂H₅ | C₃H₇-n | S | S | 87 | $n_D^{20}$:1.5209 |
| 31 | CH₃ | H | C₂H₅O |  | C₂H₅ | S | O | 82 | $n_D^{20}$:1.5482 |
| 32 | CH₃ | H | C₂H₅O | CH₃ | C₃H₇-iso | S | O | 99 | $n_D^{20}$:1.5009 |
| 33 | CH₃ | H | C₂H₅O | OC₂H₅ | C₂H₅ | O | O | 66 | $n_D^{23}$:1.4669 |
| 34 | CH₃ | H | C₂H₅O | OCH₃ | CH₃ | S | O | 80 | $n_D^{20}$:1.5111 |
| 35 | CH₃ | H | C₂H₅O | CH₃ | C₂H₅ | S | O | 86 | $n_D^{20}$:1.5080 |
| 36 | CH₃ | H | C₂H₅O | C₂H₅ | CH₃ | S | O | 89 | $n_D^{20}$:1.5106 |
| 37 | CH₃ | H | C₂H₅O | C₄H₉-sec. | C₂H₅ | S | O | 94 | $n_D^{23}$:1.5040 |
| 38 | CH₃ | H | C₂H₅O | NH—C₃H₇-iso | C₂H₅ | S | O | 87 | $n_D^{23}$:1.5042 |
| 39 | CH₃ | H | C₂H₅O | OCH₃ | C₃H₇-n | S | O | 78 | $n_D^{23}$:1.4929 |
| 40 | CH₃ | H | C₂H₅O | OC₃H₇-iso | C₃H₇-n | S | O | 83 | $n_D^{23}$:1.4856 |
| 41 | —CH₂—CH₂—CN | H | CH₃O | C₂H₅ | C₂H₅ | S | O | 89 | $n_D^{23}$:1.5130 |
| 42 | —CH₂—CH₂—CN | H | CH₃O | OC₂H₅ | C₂H₅ | S | O | 90 | $n_D^{23}$:1.4945 |
| 43 | —CH₂—CH₂—CN | H | CH₃O | OCH₃ | CH₃ | S | O | 76 | $n_D^{23}$:1.5030 |
| 44 | H | H | CH₃O | C₂H₅ | C₂H₅ | S | O | 83 | $n_D^{23}$:1.4982 |
| 45 | H | H | CH₃O | OC₂H₅ | C₂H₅ | S | O | 60 | $n_D^{23}$:1.5319 |
| 46 | H | H | CH₃O | OCH₃ | CH₃ | S | O | 67 | $n_D^{23}$:1.5321 |
| 47 |  | H | C₂H₅O | C₂H₅ | C₂H₅ | S | O | 82 | $n_D^{23}$:1.5479 |
| 48 |  | H | C₂H₅O | OC₂H₅ | C₂H₅ | S | O | 70 | $n_D^{23}$:1.5302 |
| 49 |  | H | C₂H₅O | OCH₃ | CH₃ | S | O | 82 | $n_D^{23}$:1.5500 |
| 50 |  | H | C₂H₅O | OC₂H₅ | C₃H₇-n | S | S | 68 | $n_D^{23}$:1.5495 |
| 51 | C₃H₇-iso | H | CH₃O | C₂H₅ | C₂H₅ | S | O | 85 | $n_D^{23}$:1.5347 |
| 52 | C₃H₇-iso | H | CH₃O | OC₂H₅ | C₂H₅ | S | O | 93 | $n_D^{23}$:1.5231 |
| 53 | C₃H₇-iso | H | CH₃O | OCH₃ | CH₃ | S | O | 94 | $n_D^{23}$:1.5272 |
| 54 | C₃H₇-iso | H | n-C₃H₇S | OC₂H₅ | C₂H₅ | S | O | 76 | $n_D^{23}$:1.5028 |
| 55 | C₃H₇-iso | H | n-C₃H₇S | C₂H₅ | C₂H₅ | S | O | 81 | $n_D^{23}$:1.5111 |
| 56 | CH₃ | H | CH₃S | OC₂H₅ | C₂H₅ | S | O | 71 | $n_D^{23}$:1.5200 |
| 57 | CH₃ | H | CH₃S | OC₂H₅ | C₂H₅ | O | O | 48 | $n_D^{23}$:1.4935 |
| 58 | CH₃ | H | CH₃S | OCH₃ | CH₃ | S | O | 85 | $n_D^{23}$:1.5378 |
| 59 | CH₃ | H | CH₃S |  | C₂H₅ | S | O | 73 | $n_D^{23}$:1.5770 |
| 60 | CH₃ | H | CH₃S | OC₂H₅ | C₃H₇-n | S | S | 41 | $n_D^{25}$:1.5470 |
| 61 | CH₃ | H | C₂H₅S | OC₂H₅ | C₂H₅ | S | O | 95 | $n_D^{23}$:1.5140 |
| 62 | CH₃ | H | C₂H₅S | OCH₃ | CH₃ | S | O | 89 | $n_D^{23}$:1.5309 |
| 63 | CH₃ | H | C₂H₅S | C₂H₅ | C₂H₅ | S | O | 90 | $n_D^{23}$:1.5288 |
| 64 | CH₃ | H | C₂H₅S | CH₃ | C₂H₅ | S | O | 89 | $n_D^{23}$:1.5346 |
| 65 | CH₃ | H | C₂H₅S | OC₂H₅ | C₂H₅ | O | O | 78 | $n_D^{23}$:1.4900 |
| 66 | CH₃ | H | C₂H₅O | CH₃ | CH₃ | S | O | | |

The insecticidal and acaridical activity of the compounds of this invention is illustrated by the following biotest examples in which the compounds according to the present invention are each identified by the number (given in brackets) from Example 2 and the known comparison compound has the following formula:

(A) = 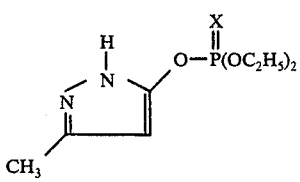

EXAMPLE 3

*Myzus* test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all of the aphids were killed whereas 0% meant that none of the aphids were killed.

The active compounds, the concentrations of the active compounds, the evaluation times and the results can be seen from the following table:

Table 3

| Active compound | (*Myzus* test) Active compound concentration in % | Degree of destruction in % after 1 day |
|---|---|---|
| (A) | 0.1 | 99 |
| | 0.01 | 40 |
| | 0.001 | 0 |
| (19) | 0.1 | 100 |
| | 0.01 | 100 |
| | 0.001 | 85 |
| (45) | 0.1 | 100 |
| | 0.01 | 100 |
| | 0.001 | 100 |
| (14) | 0.1 | 100 |
| | 0.01 | 100 |
| | 0.001 | 99 |
| (18) | 0.1 | 100 |
| | 0.01 | 100 |
| | 0.001 | 100 |
| (42) | 0.1 | 100 |
| | 0.01 | 100 |
| | 0.001 | 80 |
| (20) | 0.1 | 100 |
| | 0.01 | 100 |
| | 0.001 | 100 |
| (17) | 0.1 | 100 |
| | 0.01 | 100 |
| | 0.001 | 98 |
| (13) | 0.1 | 100 |
| | 0.01 | 100 |
| | 0.001 | 100 |
| (21) | 0.1 | 100 |
| | 0.01 | 100 |
| | 0.001 | 100 |
| (44) | 0.1 | 100 |
| | 0.01 | 100 |
| | 0.001 | 85 |
| (12) | 0.1 | 100 |
| | 0.01 | 100 |
| | 0.001 | 100 |
| (51) | 0.1 | 100 |
| | 0.01 | 100 |
| | 0.001 | 100 |
| (41) | 0.1 | 100 |
| | 0.01 | 100 |
| | 0.001 | 98 |
| (22) | 0.1 | 100 |
| | 0.01 | 100 |
| | 0.001 | 99 |
| (15) | 0.1 | 100 |
| | 0.01 | 100 |
| | 0.001 | 98 |
| (16) | 0.1 | 100 |
| | 0.01 | 100 |
| | 0.001 | 85 |
| (57) | 0.1 | 100 |
| | 0.01 | 100 |
| | 0.001 | 100 |
| (56) | 0.1 | 100 |
| | 0.01 | 100 |
| | 0.001 | 100 |
| (29) | 0.1 | 100 |
| | 0.01 | 100 |
| | 0.001 | 98 |
| (35) | 0.1 | 100 |

Table 3-continued

| Active compound | (*Myzus* test) Active compound concentration in % | Degree of destruction in % after 1 day |
|---|---|---|
| | 0.01 | 100 |
| | 0.001 | 100 |
| (32) | 0.1 | 100 |
| | 0.01 | 100 |
| | 0.001 | 99 |
| (28) | 0.1 | 100 |
| | 0.01 | 100 |
| | 0.001 | 100 |
| (36) | 0.1 | 100 |
| | 0.01 | 100 |
| | 0.001 | 95 |
| (27) | 0.1 | 100 |
| | 0.01 | 100 |
| | 0.001 | 100 |
| (39) | 0.1 | 100 |
| | 0.01 | 100 |
| | 0.001 | 70 |
| (30) | 0.1 | 100 |
| | 0.01 | 100 |
| | 0.001 | 98 |
| (65) | 0.1 | 100 |
| | 0.01 | 100 |
| | 0.001 | 100 |
| (61) | 0.1 | 100 |
| | 0.01 | 100 |
| | 0.001 | 100 |
| (64) | 0.1 | 100 |
| | 0.01 | 100 |
| | 0.001 | 70 |
| (63) | 0.1 | 100 |
| | 0.01 | 100 |
| | 0.001 | 100 |
| (2) | 0.1 | 100 |
| | 0.01 | 100 |
| | 0.001 | 100 |
| (8) | 0.1 | 100 |
| | 0.01 | 100 |
| | 0.001 | 70 |
| (5) | 0.1 | 100 |
| | 0.01 | 100 |
| | 0.001 | 100 |
| (4) | 0.1 | 100 |
| | 0.01 | 100 |
| | 0.001 | 70 |
| (1) | 0.1 | 100 |
| | 0.01 | 100 |
| | 0.001 | 100 |
| (10) | 0.1 | 100 |
| | 0.01 | 100 |
| | 0.001 | 90 |
| (9) | 0.1 | 100 |
| | 0.01 | 100 |
| | 0.001 | 100 |
| (6) | 0.1 | 100 |
| | 0.01 | 100 |
| | 0.001 | 70 |
| (50) | 0.1 | 100 |
| | 0.01 | 100 |
| | 0.001 | 85 |

EXAMPLE 4

*Tetranychus* test (resistant)
Solvent: 3 parts by weight of acetone
Emulsifier: 1 part by weight of alklylaryl polyglycol ether To produce a suitable separation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 4

(Tetranychus test)

| Active compound | Active compound concentration in % | Degree of destruction in % after 2 days |
|---|---|---|
| (A) | 0.1 | 50 |
| | 0.01 | 0 |
| (20) | 0.1 | 100 |
| | 0.01 | 98 |
| (17) | 0.1 | 100 |
| | 0.01 | 80 |
| (13) | 0.1 | 100 |
| | 0.01 | 90 |
| (56) | 0.1 | 100 |
| | 0.01 | 70 |
| (29) | 0.1 | 100 |
| | 0.01 | 60 |
| (35) | 0.1 | 100 |
| | 0.01 | 100 |
| (32) | 0.1 | 100 |
| | 0.01 | 70 |
| (28) | 0.1 | 100 |
| | 0.01 | 60 |
| (61) | 0.1 | 100 |
| | 0.01 | 60 |
| (64) | 0.1 | 100 |
| | 0.01 | 80 |
| (63) | 0.1 | 100 |
| | 0.01 | 40 |
| (2) | 0.1 | 100 |
| | 0.01 | 98 |
| (8) | 0.1 | 100 |
| | 0.01 | 99 |
| (5) | 0.1 | 100 |
| | 0.01 | 99 |
| (4) | 0.1 | 100 |
| | 0.01 | 70 |
| (9) | 0.1 | 100 |
| | 0.01 | 80 |

EXAMPLE 5

Test insects Blatta orientalis
Solvent: Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of the active compound. About 25 test insects were then placed in the Petri dish and it was covered with a glass lid.

The condition of the test insects was observed 3 days after the commencement of the experiments. The destruction, in %, was determined. 100% denoted that all of the test insects had been killed; 0% denoted that none of the test insects had been killed.

The active compounds, the concentrations of the active compounds, and the results can be seen from the following table:

Table 5

(Blatta orientalis)

| Active compound | Active compound concentration of the solution in % | Degree of destruction in % |
|---|---|---|
| (A) | 0.02 | 0 |
| (14) | 0.02 | 100 |
| (22) | 0.02 | 100 |
| (24) | 0.02 | 100 |
| (21) | 0.02 | 100 |
| (12) | 0.02 | 100 |
| (17) | 0.02 | 100 |
| (52) | 0.02 | 100 |
| (51) | 0.02 | 100 |
| (35) | 0.02 | 100 |
| (32) | 0.02 | 100 |
| (27) | 0.02 | 100 |

EXAMPLE 6

Test insects Sitophilus granarius
Solvent: Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petric dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denoted that all of the test insects had been killed; 0% denoted that none of the test insects had been killed.

The active compounds, the concentrations of the active compounds, and the results can be seen from the following table:

Table 6

(Sitophilus granarius)

| Active compound | Active compound concentration of the solution in % | Degree of destruction in % |
|---|---|---|
| (A) | 0.02 | 0 |
| (14) | 0.02 | 100 |
| (22) | 0.02 | 100 |
| (24) | 0.002 | 100 |
| (21) | 0.002 | 100 |
| (20) | 0.02 | 100 |
| (12) | 0.02 | 100 |
| (17) | 0.02 | 100 |
| (15) | 0.02 | 100 |
| (13) | 0.02 | 100 |
| (16) | 0.02 | 100 |
| (53) | 0.02 | 100 |
| (52) | 0.002 | 100 |
| (51) | 0.002 | 100 |
| (42) | 0.02 | 100 |
| (41) | 0.02 | 100 |
| (29) | 0.02 | 100 |
| (33) | 0.02 | 100 |
| (39) | 0.02 | 100 |
| (36) | 0.02 | 100 |
| (35) | 0.02 | 100 |
| (32) | 0.02 | 100 |
| (28) | 0.02 | 100 |
| (27) | 0.02 | 100 |
| (31) | 0.02 | 100 |
| (49) | 0.02 | 100 |
| (48) | 0.02 | 100 |
| (47) | 0.02 | 100 |

Table 6-continued
(Sitophilus granarius)

| Active compound | Active compound concentration of the solution in % | Degree of destruction in % |
| --- | --- | --- |
| (2) | 0.02 | 100 |
| (1) | 0.02 | 100 |
| (5) | 0.02 | 100 |
| (6) | 0.02 | 100 |
| (4) | 0.02 | 100 |
| (61) | 0.02 | 100 |
| (63) | 0.02 | 100 |
| (64) | 0.02 | 100 |
| (65) | 0.02 | 100 |
| (56) | 0.02 | 100 |
| (57) | 0.02 | 100 |

EXAMPLE 7

Test with parasitic scab mites (Psoroptes cuniculi)
Solvent: Cremophor

To produce a suitable preparation of active compound, the active substance in question was mixed with the stated solvent in the ratio of 1:2 and the concentrate thus obtained was diluted with water to the desired concentration.

About 10–25 scab mites (Psoroptes cuniculi) were introduced into 1 ml portions of the active compound preparation to be tested, which had been pipetted into the tablet nests of a blister pack. After 24 hours, the degree of destruction in percent was determined. 100% meant that all of the mites had been killed and 0% meant that none of the mites had been killed.

Active compounds, active compound concentrations and results can be seen from the table which follows:

Table 7
(Test with parasitic scab mites)
(Psoroptes cuniculi)

| Active compound | Active compound concentration in ppm | Degree of destruction in % |
| --- | --- | --- |
| (30) | 1,000 | 100 |
|  | 300 | 100 |
|  | 100 | 100 |
|  | — | — |
| (35) | 1,000 | 100 |
|  | 300 | 100 |
|  | 100 | 100 |
|  | — | — |

EXAMPLE 8

Test with parasitic fly larvae
Solvent: 35 parts by weight of ethylene polyglycol monomethyl ether
Emulsifier: 35 parts by weight of nonylphenol polyglycol ether To produce a suitable preparation of active compound, 30 parts by weight of the active substance in question were mixed with the stated amount of solvent which contained the above-mentioned proportion of emulsifier and the concentrate thus obtained was diluted with water to the desired concentration.

About 20 fly larvae (Lucilia cuprina) were introduced into a test tube which contained about 2 ml of horse muscle. 0.5 ml of the preparation of active compound was applied to this horse meat. After 24 hours, the degree of destruction in % was determined. 100% meant that all of the larvae had been killed and 0% meant that none of the larvae had been killed.

The active compound, the concentrations of the active compound and the results can be seen from the table which follows:

Table 8
(Test with parasitic fly larvae (Lucilia cuprina res.))

| Active compound | Active compound concentration in ppm | Degree of destruction in % |
| --- | --- | --- |
| (37) | 1,000 | 100 |
|  | 100 | 100 |
|  | — | — |

It will be appreciated that the instant specification and claims are set forth by way of illustration and not limitation, and that various modifications and changes may be made without departing from the spirit and scope of the present invention.

What is claimed is:

1. A compound of the formula in which

R is hydrogen, alkyl with 1 to 6 carbon atoms, cyanoalkyl with 1 to 4 carbon atoms in the alkyl part or phenyl, $R^1$ is hydrogen or halogen, $R^2$ is alkoxy or alkylthio each with 1 to 6 carbon atoms, $R^3$ is alkyl, alkoxy or monoalkylamino each with 1 to 6 carbon atoms, or phenyl, $R^4$ is alkyl with 1 to 6 carbon atoms, and X and Y each independently is oxygen or sulphur.

2. A compound according to claim 1, in which $R^1$ is hydrogen or chlorine, and

X is sulphur.

3. A compound according to claim 1, wherein such compound is O,O-diethyl-O-[1-methyl-3-n-propylthiomethylpyrazol(5)yl]-thionophosphoric acid ester of the formula 4. A compound according to claim 1, wherein such compound is O,O-diethyl-O-[1-methyl-3-methoxymethylpyrazol(5)yl]-thionophosphoric acid ester of the formula 5. A compound according to claim 1, wherein such compound is O,O-diethyl-O-[1-methyl-3-ethoxymethyl-pyrazol(5)yl]-thionophosphoric acid ester of the formula

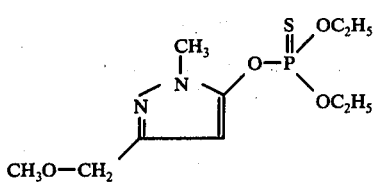

6. A compound according to claim 1, wherein such compound is O,O-diethyl-O-[3-methoxymethyl-pyrazol(5)yl]-thionophosphoric acid ester of the formula

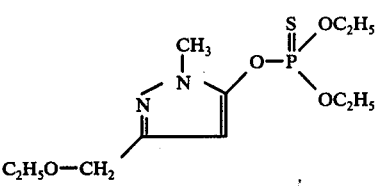

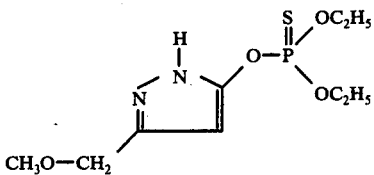

7. A compound according to claim 1, wherein such compound is O,O-diethyl-O-[1-methyl-3-ethylthiomethylpyrazol(5)yl]-thionophosphoric acid ester of the formula

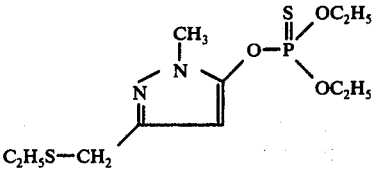

8. An arthropodicidal composition containing as active ingredient an arthropodicidally effective amount of a compound according to claim 1 in admixture with a diluent.

9. A method of combating arthropods which comprises applying to said arthropods, or to a habitat thereof, an arthropodicidally effective amount of a compound according to claim 1.

10. The method according to claim 9 in which said compound is
O,O-diethyl-O-[1-methyl-3-n-propylthiomethyl-pyrazol(5)yl]-thionophosphoric acid ester,
O,O-diethyl-O-[1-methyl-3-methoxymethylpyrazol(5)yl]-thionophosphoric acid ester,
O,O-diethyl-O-[1-methyl-3-ethoxymethylpyrazol(5)yl]-thionophosphoric acid ester,
O,O-diethyl-O-[3-methoxymethylpyrazol(5)yl]-thionophosphoric acid ester, or
O,O-diethyl-O-[1-methyl-3-ethylthiomethylpyrazol(5)yl]-thionophosphoric acid ester.

* * * * *